United States Patent
Sugiyama et al.

(10) Patent No.: US 6,371,668 B1
(45) Date of Patent: Apr. 16, 2002

(54) PRINTING DATA TRANSFER METHOD AND PRINTER

(75) Inventors: Yuichi Sugiyama; Michitaka Fukuda, both of Tokyo (JP)

(73) Assignee: Copyer Co., Ltd., Tokyo (JP)

( * ) Notice: Subject to any disclaimer, the term of this patent is extended or adjusted under 35 U.S.C. 154(b) by 0 days.

(21) Appl. No.: 09/530,615
(22) PCT Filed: Sep. 10, 1999
(86) PCT No.: PCT/JP99/04940
  § 371 Date: May 1, 2000
  § 102(e) Date: May 1, 2000
(87) PCT Pub. No.: WO00/15438
  PCT Pub. Date: Mar. 23, 2000

(30) Foreign Application Priority Data
  Sep. 10, 1998 (JP) ............................................ 10-274379

(51) Int. Cl.[7] .................................................. B41J 5/30
(52) U.S. Cl. .............................. 400/61; 400/70; 400/76
(58) Field of Search .............................. 400/61, 70, 76, 400/279, 283

(56) References Cited

FOREIGN PATENT DOCUMENTS

EP  0 499 288 A2  *  8/1992
JP  6-270472  9/1994

* cited by examiner

Primary Examiner—John S. Hilten
Assistant Examiner—Charles H. Nolan, Jr.
(74) Attorney, Agent, or Firm—Dellett and Walters

(57) ABSTRACT

In order to reduce the number of signal lines of the cable between the controller and the carriage and to allow the print timing of each head to be adjusted in increments smaller than one pixel, the signal lines include a line for carrying serial print data to be supplied to a plurality of print heads in a predetermined order, a line for carrying a clock signal corresponding to individual bits of the data, lines for carrying signal HDSEL[1 . . . 0] indicating which print head corresponds to which print data included in the serial print data, and lines for driving the heads. When data is transferred over this cable, one slice section is divided into a plurality of sections, the slice section corresponding to a time slot required to transfer a unit of print data corresponding to a plurality of dot printing elements of the plurality of heads, each divided section is further divided into a number of subsections the number of which is equal to the number of the print heads. The transfer of the print data of each print head is started independently of the print data of other print heads, beginning with its arbitrary subsection.

11 Claims, 22 Drawing Sheets

FIRST CONVENTIONAL CONNECTION METHOD

PRINTING DATA TRANSFER METHOD AND PRINTER

TECHNICAL FIELD

The present invention relates to a printing apparatus such as a printer or a plotter, and more particularly to the optimization of a method for transferring data to a print head having a shift register installed therein.

BACKGROUND ART

Normally, a printing apparatus, such as an ink jet printer or plotter, repeats printing and paper sheet feeding to complete an image while moving the print head across the paper sheet.

To send print data to the print head carried on the carriage, the data is sent from a central processor (engine controller), which controls the printing apparatus, to the print head via a cable.

With the introduction of a full-color, high-speed printing apparatus, more heads are installed in the apparatus, usually four and, in some cases, six. This requires more signal lines between the central processor and the carriage, increasing both the apparatus size and the cost.

In addition, because of the use of a flexible flat cable, more signal lines not only increase the cost but make the radiation noise problem more serious. Therefore, there is a need for minimizing the number of signal lines.

FIGS. 17 and 18 show examples of a conventional method for connection between the engine controller and the carriage. In the conventional method shown in FIG. 17, the largest number of signal lines is used because all data for each head are transferred independently to each print head.

On the other hand, in a conventional method shown in FIG. 18, head data (HDDATA) and drive signals (HDDRIVE) are sent independently to each head while a data transfer clock (HDCLK) and a latch clock (HDLTCLK) are shared by the heads. This configuration uses less signal lines than the configuration shown in FIG. 17. However, as shown in the timing chart in FIG. 19, 128 bits of data are continuously sent to one head and 128 bits of data are latched at the same time in the configuration shown in FIG. 18. In this configuration, data is transferred to each head, one slice at a time and, therefore, fine print timing adjustment cannot be made. (In this specification, a "slice" represents a group of pixels of the number of one-horizontal-pixel by vertical print nozzles (128 pixels in this case), as one unit. A slice corresponds to a time slot required to transfer a unit of print data corresponding to a plurality of print nozzles on a plurality of heads). Thus, when printing data in color, color mixture adjustment is made by one dot. Because human eye can normally identify a color difference of up to 1/4 pixel, it is known that adjustment of 1/4 pixel or less is needed to avoid a problem.

Therefore, it is an object of the present invention to provide a print data transfer method and printing apparatus that reduce the number of signal lines used in the cable between the printing apparatus controller and the carriage and that can adjust the print timing of each head by less than one pixel.

DISCLOSURE OF INVENTION

The print data transfer method according to the present invention is a method for transferring print data from a controller to a carriage via a cable for use in a printing apparatus which performs printing while moving the carriage bi-directionally over a sheet of paper, the carriage carrying thereon a plurality of print heads each having a plurality of dot printing elements, wherein the cable comprises a signal line via which serial print data to be supplied to the plurality of print heads is transferred in a predetermined order, a signal line via which a clock signal corresponding to individual bits of the serial print data is transferred, signal lines via which a signal indicating which print head corresponds to which print data included in the serial print data is transferred, and signal lines via which drive signals of the heads are transferred, the method comprising the steps of dividing one slice section into a plurality of sections, the slice section corresponding to a time slot required to transfer a unit of print data corresponding to the plurality of dot printing elements of the plurality of heads and further dividing each divided section into a number of subsections, the number being equal to the number of the print heads; assigning the different subsections of each divided section to the plurality of print heads; dividing the unit of print data for each print head into the number of the plurality of divided sections; and starting a transfer of the print data of each print head independently of the print data of other print heads, beginning with any one of the plurality of subsections assigned to that particular print head in one slice section.

According to the present invention, because print data for the plurality of print heads is converted to serial data for transfer over the cable, the number of signals in the cable can be reduced. At the same time, one slice section is divided into a plurality of sections, each of these divided sections is further divided into a number of subsections, the number being equal to the number of the print heads, and the different subsections of each divided section are assigned to the plurality of print heads. This enables the print timing of each print head to be adjusted in increments of less than one pixel. As a result, this minimizes color misalignment in color printing and ruled-line misalignment caused by misalignment of the heads.

In the above printing apparatus, for example, four print heads are used as the plurality of print heads, the one slice section is divided at least into four divided sections, and each divided section is further divided into four subsections.

The apparatus for implementing the method according to the present invention is a printing apparatus which performs printing while moving a carriage bi-directionally over a sheet of paper, the carriage carrying thereon a plurality of print heads each having a plurality of dot printing elements, the printing apparatus comprising a controller for generating serial print data including print data for the plurality of print heads in a predetermined order, a clock signal corresponding to individual bits of the serial print data, a signal indicating which print head corresponds to which print data included in the serial print data, and a drive signal of each head; a cable for transferring the serial print data and various signals generated by the controller to the carriage; and a signal distributing means for distributing the print data and the various signals received from the cable to the plurality of print heads, wherein the controller divides one slice section into a plurality of sections, the slice corresponding to a time slot required to transfer a unit of print data corresponding to the plurality of dot printing elements of the plurality of heads; further divides each divided section into a number of subsections, the number being equal to the number of the print heads; assigns the different subsections of each divided section to the plurality of print heads; divides the unit of print data for each print head into the number of the plurality of divided sections; and starts a transfer of the print data of each print head independently of the print data of other print heads, beginning with a specified subsection of the plurality of subsections assigned to that particular print head in the divided section.

More specifically, each print head has a plurality of dot print means arranged in a direction substantially perpendicular to a carriage moving direction and the print data for the plurality of dot print means of one print head is transferred using the plurality of subsections assigned to that particular print head.

BEST MODE FOR CARRYING OUT THE INVENTION

Preferred embodiments of a printing apparatus according to the present invention will now be described in detail by referring to the attached drawings. An ink jet printing apparatus is raised here as an example.

Figure 1:
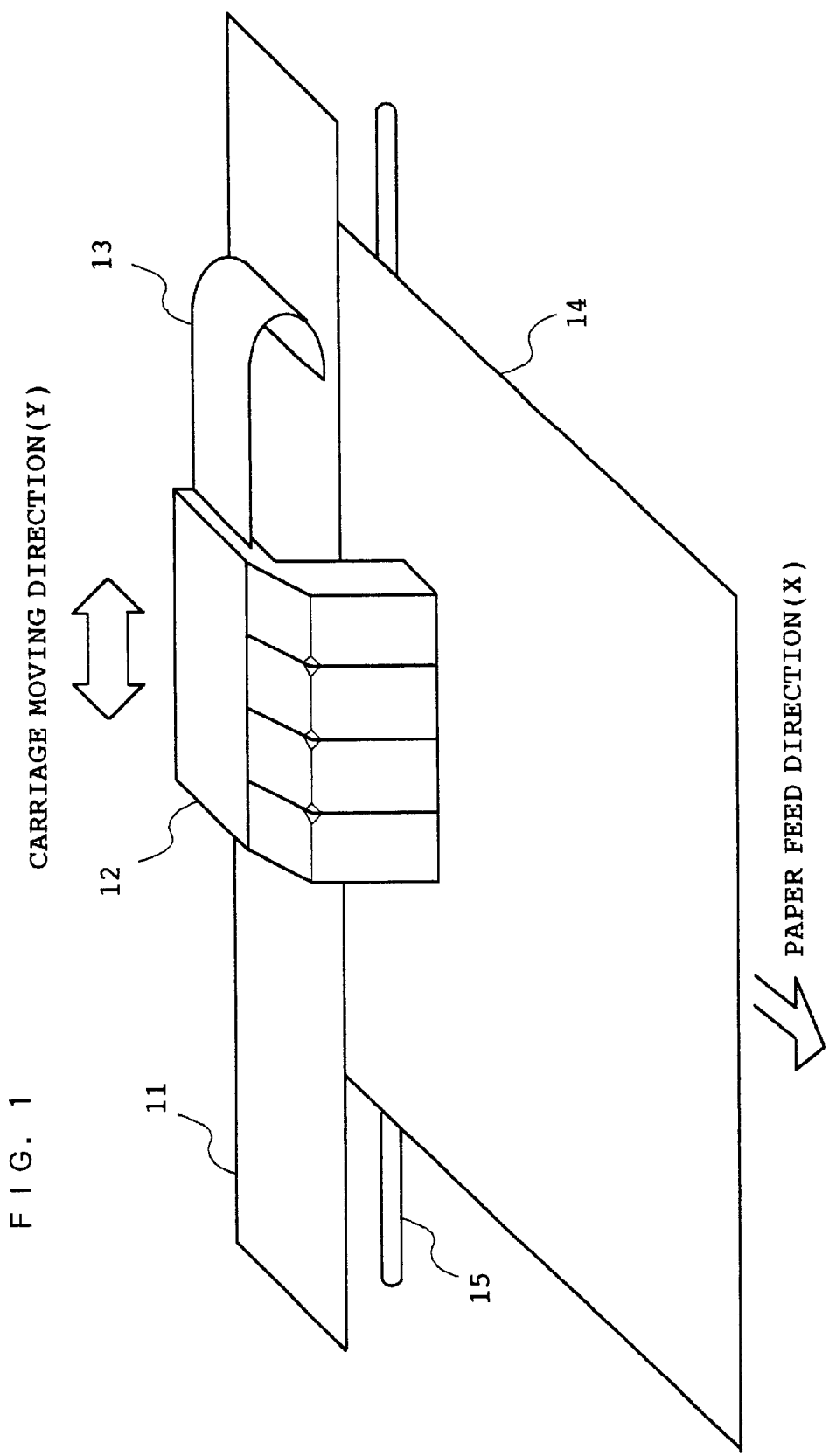
FIG. 1 is an external view showing a portion around the print unit of a printing apparatus in an embodiment of the present invention.
Figure 2:
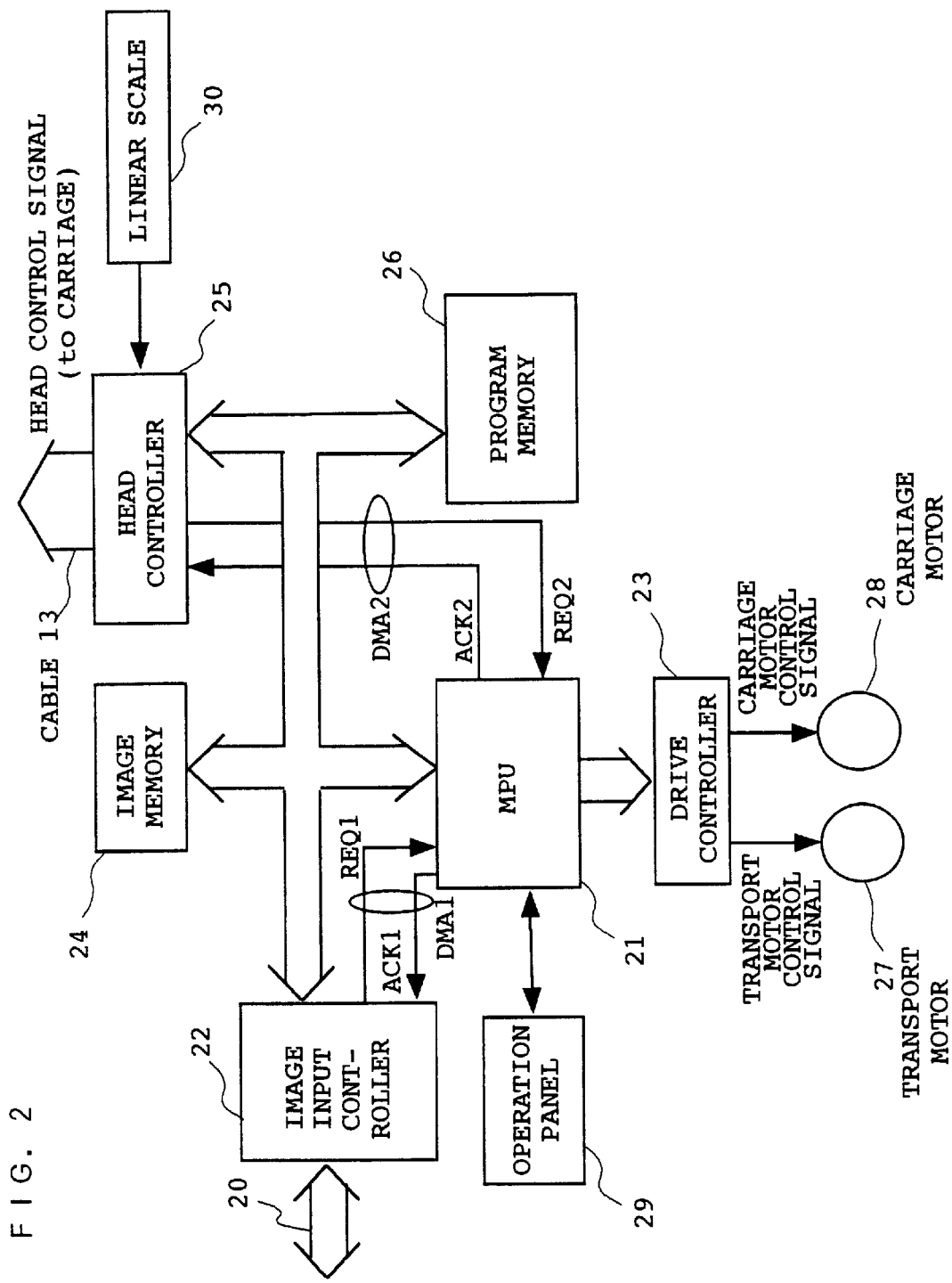
FIG. 2 is a control block diagram showing an engine controller of the printing apparatus shown in FIG. 1.

FIG. 1 shows an external view of the portion around a printing unit of the printing apparatus in an embodiment. A carriage 12 carries thereon four (Y, M, C, K) color print heads. The carriage 12 moves, along a carriage support rail 11, back and forth in the direction (Y) which is perpendicular to the feed direction (X) of a paper sheet 14. Each head, with 128 print nozzles (dot print elements) arranged substantially in the X direction, has a register (128-bit shift register) corresponding to these nozzles. Power and various signals supplied to the heads are transferred from an engine controller via a flexible flat cable (FFC) 13. The carriage 12 performs a printing on the sheet 14, moving bi-directionally leftwards and rightwards. Each time one band of data extending in the carriage scan direction (Y direction) has been printed, a sheet transport roller 15 moves the sheet in the X direction by a predetermined amount. Repeating such an operation completes the entire image on one sheet of paper. FIG. 2 shows a control block of the engine controller.

With reference to FIG. 2, an explanation will be given of an operation from an acceptance of image data to a transfer thereof to the print heads. First, an image input controller 22 accepts image data via an external interface 20. Then, the image input controller 22 immediately issues a DMA request (REQ1) to an MPU 21. In response, the MPU 21 transfers the image data to an image memory 24 in the DMA mode and, at the same time, outputs a DMA acknowledge (ACK1) to the image input controller 22. The MPU 21 also transfers the image data to a head controller 25 to start a printing. The head controller 25 transfers print data to the heads according to the count value of a linear scale signal entered in synchronization with the carriage movement and, at the same time, gives print pulses to the heads to print the image data.

When the image data in the head controller 25 is exhausted, the head controller 25 requests the MPU 21 to transfer image data (REQ2). In response, the MPU 21 transfers image data stored in the image memory 24 to the head controller 25 in the DMA mode and, at the same time, outputs a DMA acknowledge (ACK2) to the head controller 25. By repeating such an operation, image data is sent to the print heads and is printed.

The MPU 21 controls a transport motor 27 and a carriage motor 28 via a drive controller 23. In addition, the MPU 21 accepts input data from, and outputs display data to, an operation panel 29.

The operation of the MPU 21, described above, is controlled by a program stored in a program memory 26 such as an ROM.

Figure 3:
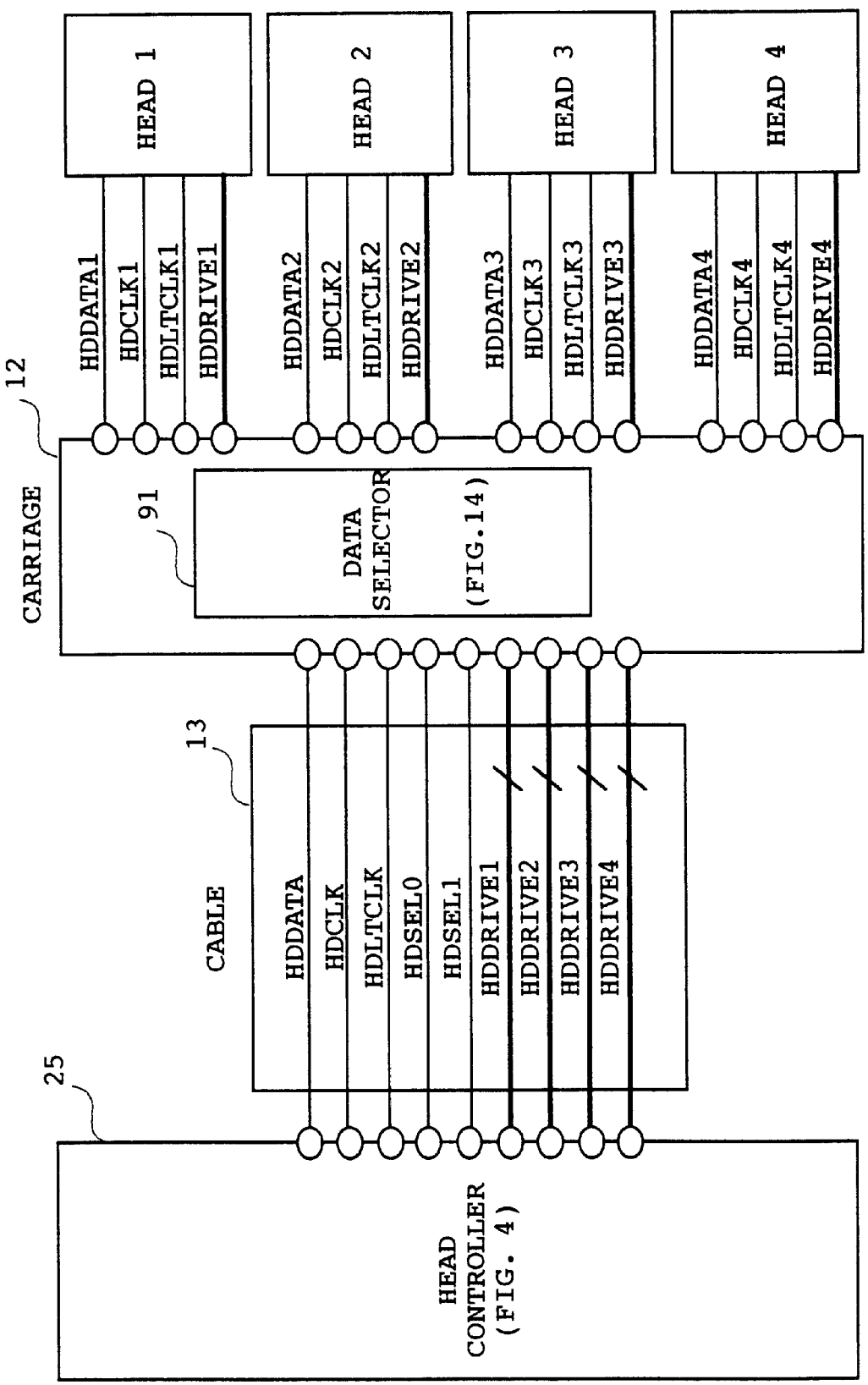
FIG. 3 is an illustration of the signals in a cable 13 connecting a head controller 25 and a carriage 12 of the printing apparatus shown in FIG. 1.
Figure 18:
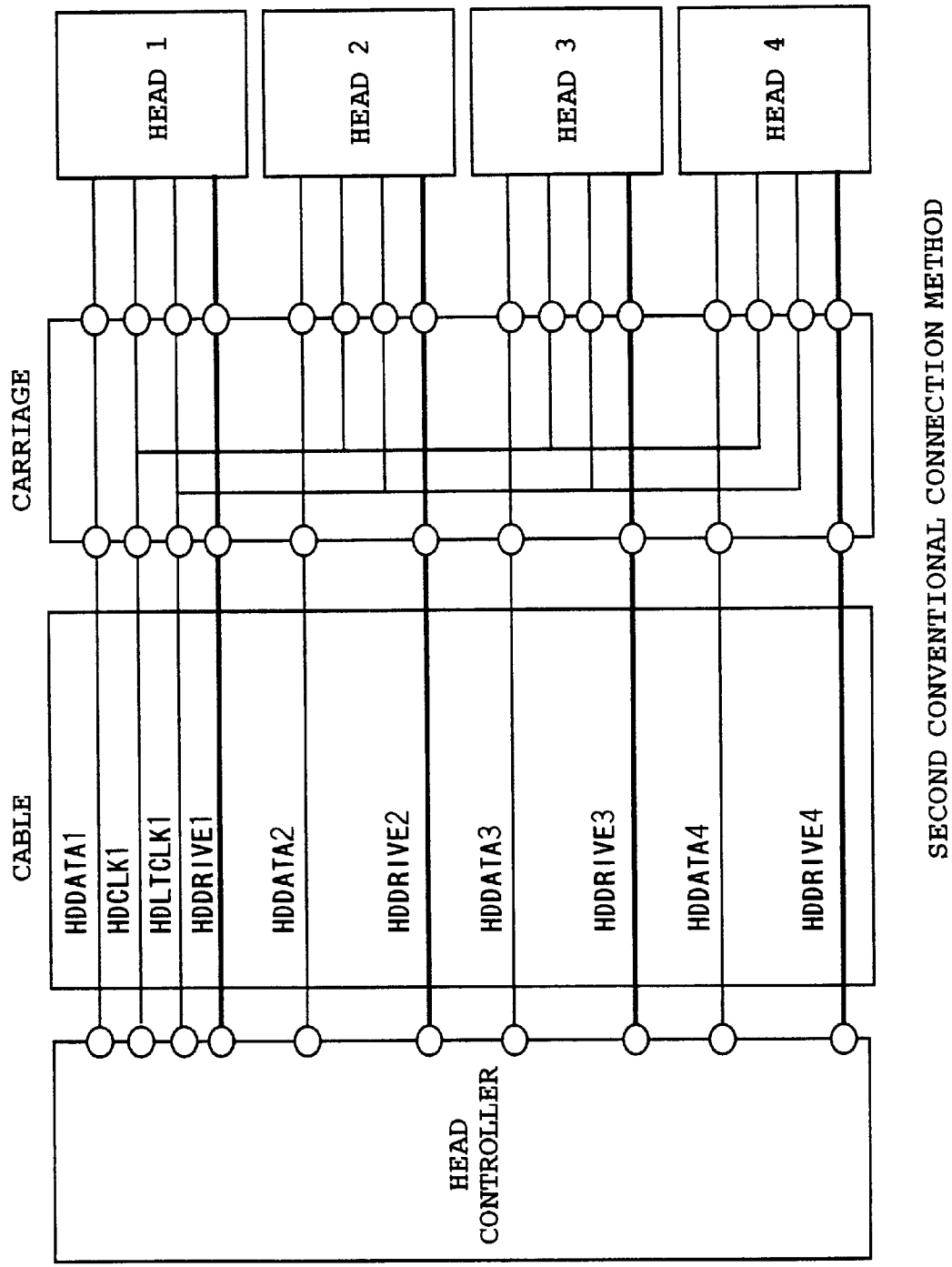
FIG. 18 is an illustration of a second example of the conventional connection between the engine controller and the carriage.
Figure 19:
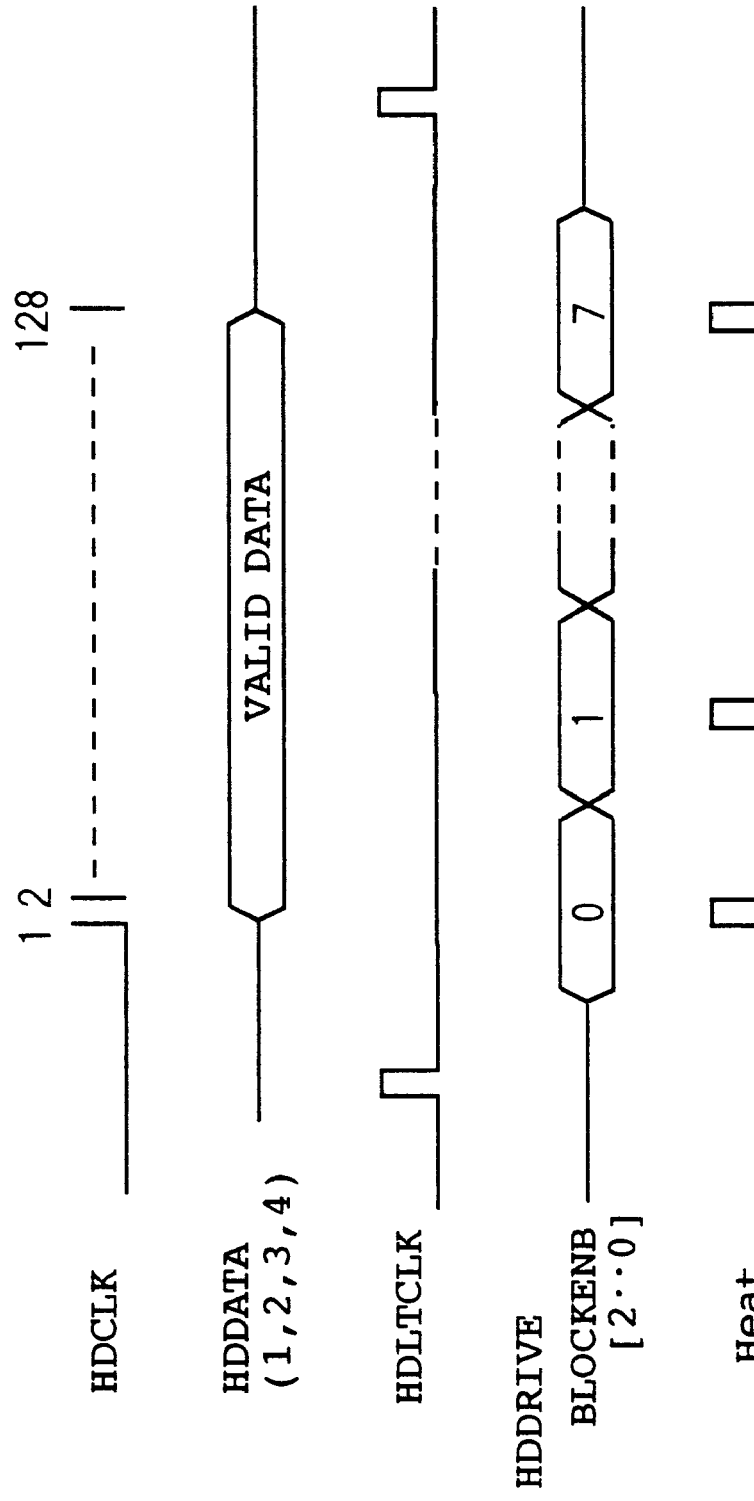
FIG. 19 is a timing diagram of head control in the conventional connection shown in FIG. 18.

FIG. 3 shows the signals sent via the cable 13 that connects the signals from the head controller 25 to the carriage 12. The signals sent via the cable 13 includes the print data HDDATA for a plurality of print heads, a data transfer clock HDCLK, a latch clock HDLTCLK, a head selection signal HDSEL0 and HDSEL1, and head drive signals HDDRIVE1, HDDRIVE2, HDDRIVE3, and HDDRIVE4. Compared with the prior art system shown in FIG. 18, it is apparent that the number of HDDATA signal lines has reduced from four to one and, at the same time, two HDSEL lines are added. In addition, as will be described later, the control in accordance with the present invention allows the print timing of each head to be adjusted by a unit smaller than one horizontal pixel. This minimizes color misalignment in color printing and ruled-line misalignment caused by misalignment of the heads.

Figure 4:
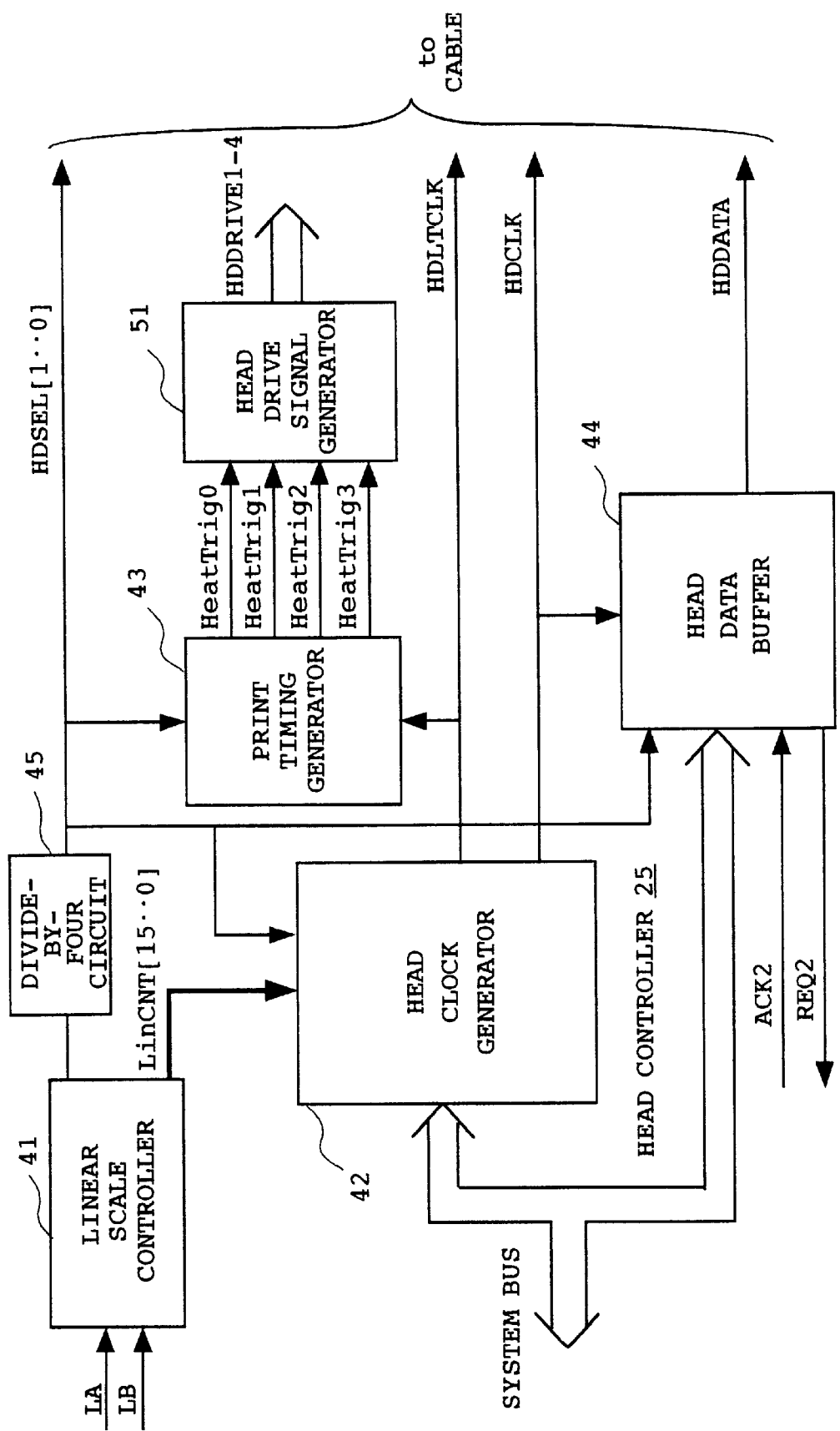
FIG. 4 is a block diagram showing an example of the internal configuration of the head controller 25 shown in FIG. 3.
Figure 5:
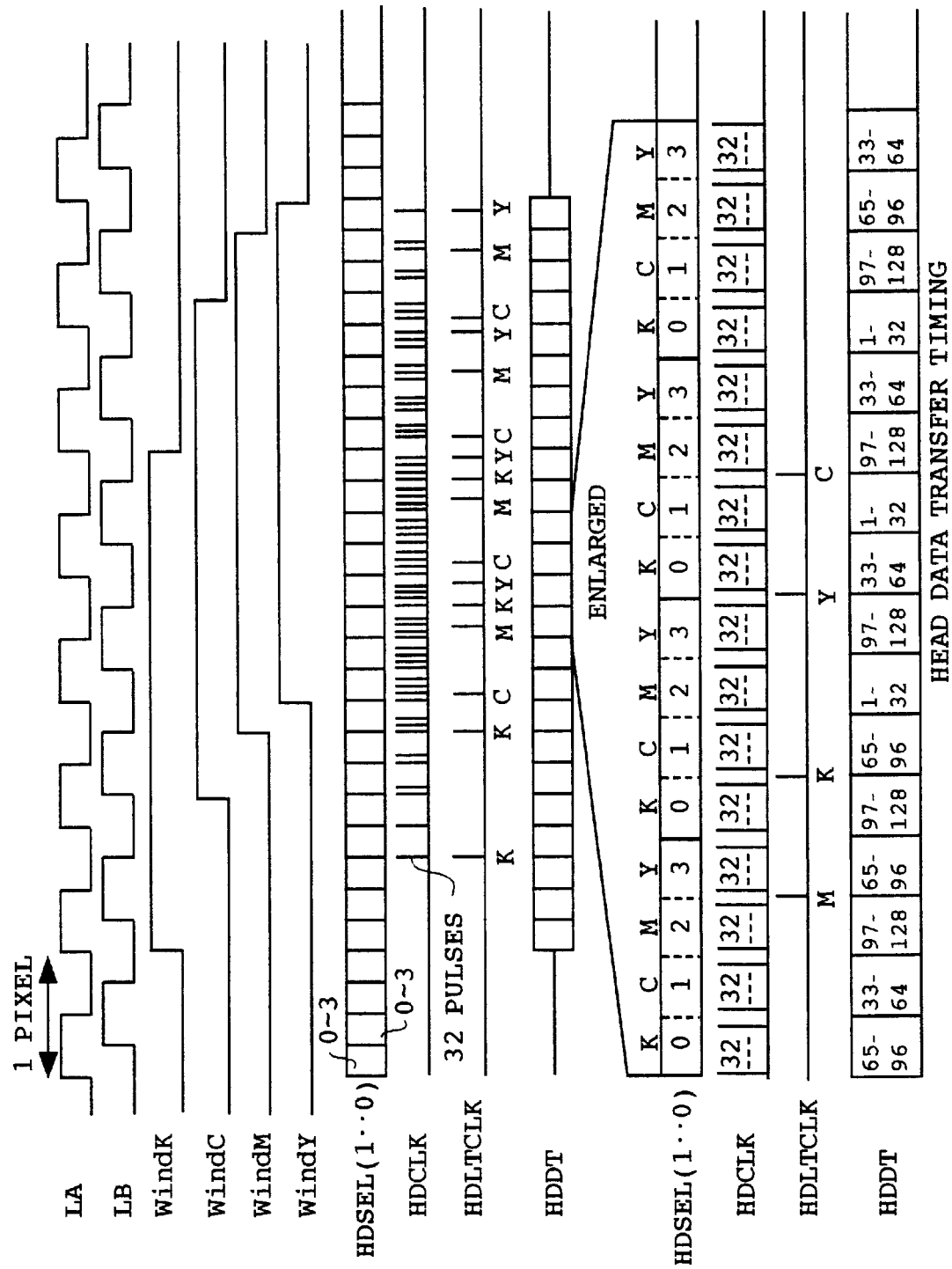
FIG. 5 is a timing diagram of head data transfer in the embodiment of the present invention.

Next, FIG. 4 shows an example of the internal configuration of the head controller 25 shown in FIG. 3. FIG. 5 is a timing diagram of head data transfer in the embodiment of the present invention. This diagram will be referenced in the description below as necessary.

The head controller 25 shown in FIG. 4 comprises a linear scale controller 41, a head clock generator 42, a print timing generator 43, a head data buffer 44, and a head drive signal generator 51.

The linear scale controller 41 generates a two-bit signal which divides one horizontal slice section into four, based on the linear scale signal (LA, LB) which are 90 degrees out of phase with each other. A divide-by-four circuit 45 generates a signal which further divides each divided section into four (00, 01, 10, and 11 in binary notation). This signal, called a head selection signal, is represented as HDSEL[1 . . . 0]. The notation [1 . . .0] indicates that the signal is a two-bit signal including bit 0 to bit 1. The divide-by-four circuit 45, which includes therein an internal timer, further divides one divided section into four subsections. That is, in this embodiment, one horizontal slice section is divided into 16 subsections. In addition, to calculate the print start position and the print end position in the carriage scan direction of each head, a 16-bit linear scale signal count value (LinCNT [15 . . . 0]) is output. This is applied to the head clock generator 42.

The head clock generator 42, print timing generator 43, head drive signal generator 51, and the head data buffer 44, shown in FIG. 4, will be detailed below.

Figure 6:
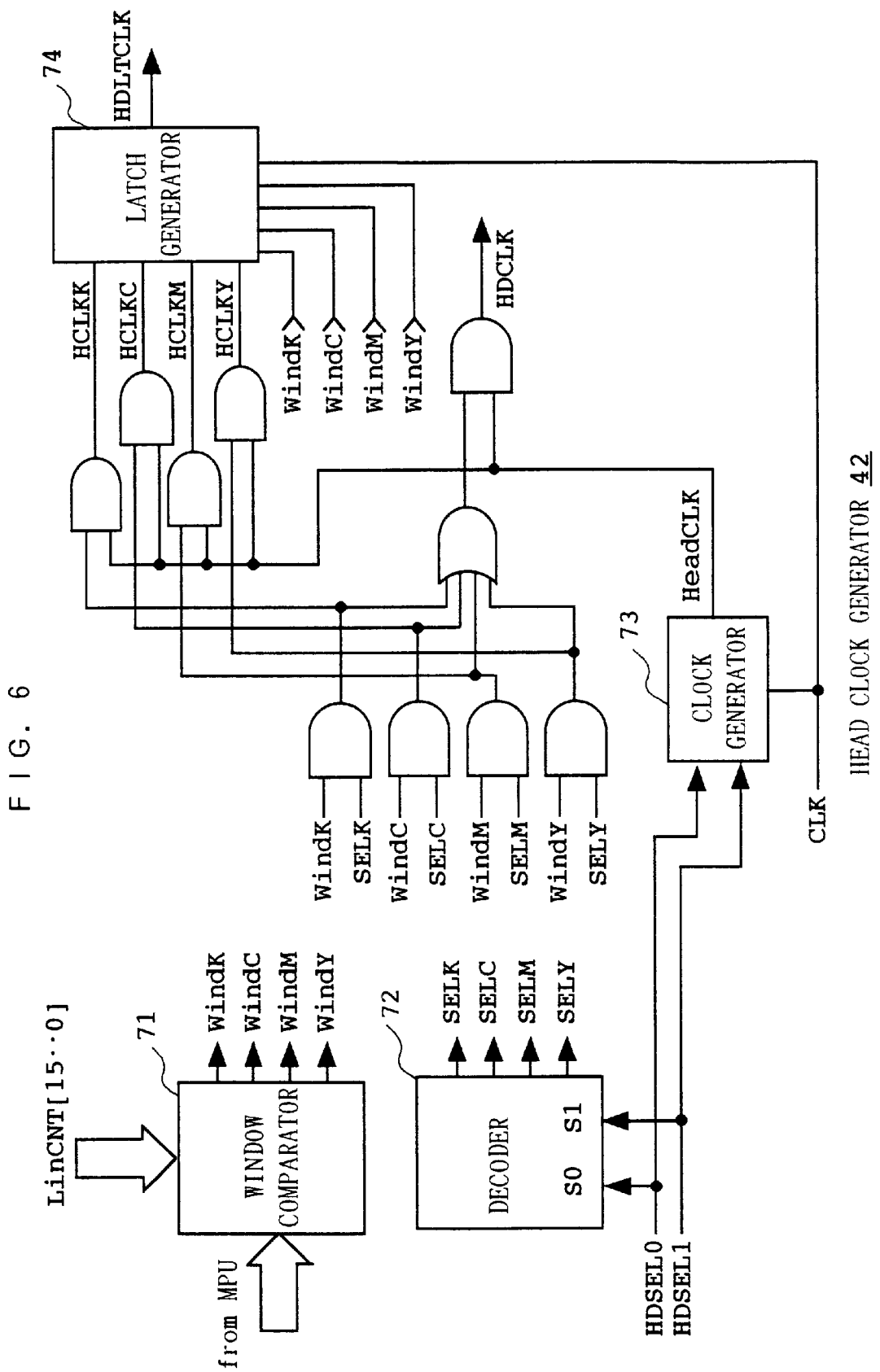
FIG. 6 is a block diagram showing an example of the configuration of a head clock generator 42 shown in FIG. 4.

FIG. 6 shows the details of the head clock generator 42. Upon receiving the print start and end positions (each may be set in increments of 1/4 pixel) of each head from the MPU 21, the head clock generator 42 compares these positions with LinCNT by using a window comparator 71 to output window signals WindK, WindC, WindM, and WindY each of which indicates the print area (period) of each head. In the timing diagram shown in FIG. 5, the period during which each window signal is high is the print area of the head. The clock generator 42 also generates the selection control signals SELK, SELC, SELM, and SELY with the use of a decoder 72 each time the head selection signal HDSEL0 and HDSEL1 changes. Also, each time the HDSEL0 and HDSEL1 change, a clock generator 73 outputs 32 clock pulses. Based on these signals, logical circuits shown at the upper-right corner of FIG. 6 generate the data transfer clock HDCLK. In addition, a latch generator 74 outputs HDLT-CLK each time the number of HeadCLK (that is, HCLK) clock pulses selected based on the HDSEL reaches 128.

Figure 7:
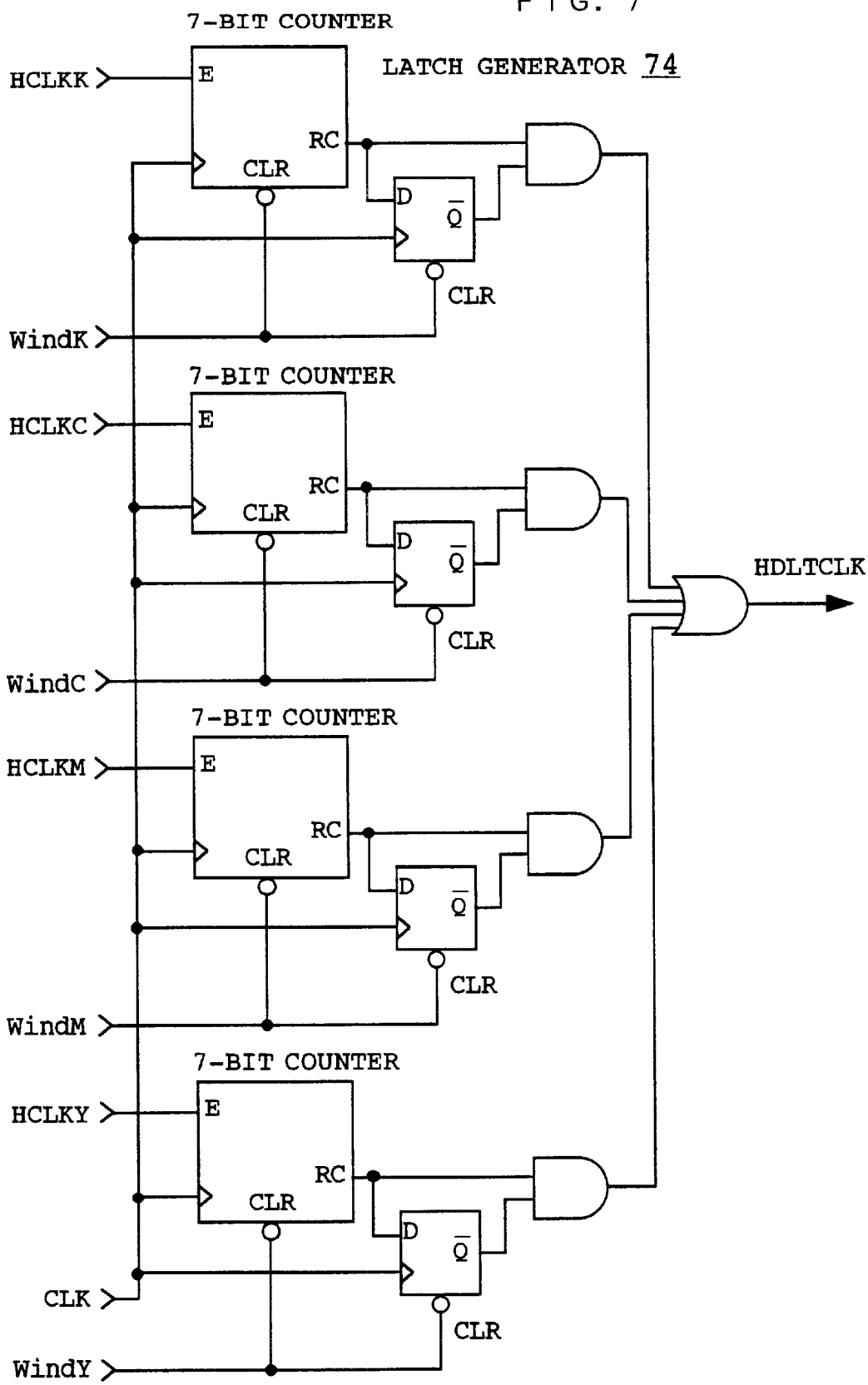
FIG. 7 is a block diagram showing an example of the configuration of a latch generator 74 shown in FIG. 6.
Figure 8:
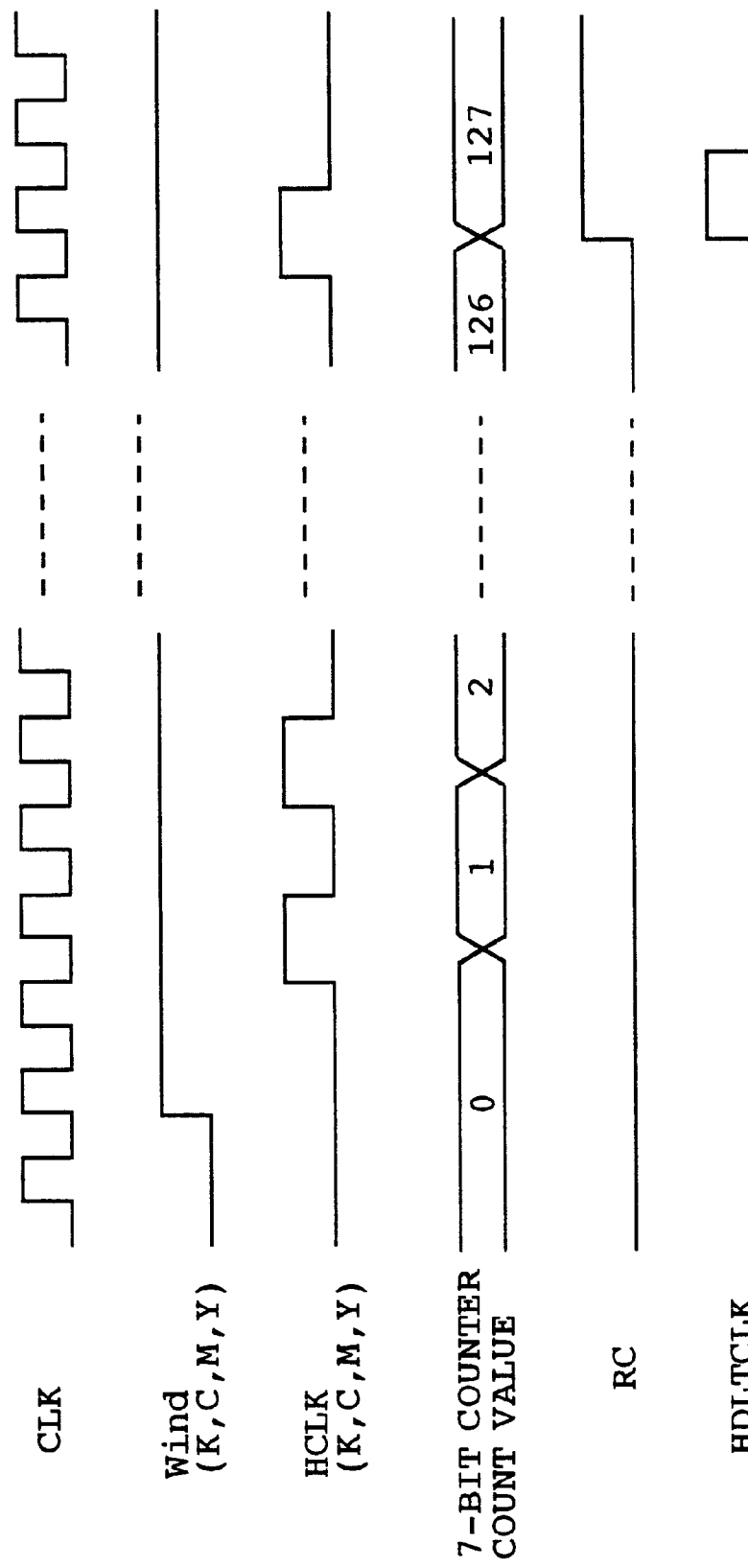
FIG. 8 is a timing diagram illustrating the operation of the latch generator 74 shown in FIG. 7.

FIG. 7 shows an example of the configuration of the latch generator 74 shown in FIG. 6. The latch generator 74 comprises plural sets of a 7-bit counter, a D flip-flop, and an AND gate for the respective heads and one OR gate shared by all the AND gates. Each time 128 HCLK clock pulses are output for each head, the latch generator 74 outputs the latch clock LTCLK. This operation is as shown in the waveform diagram in FIG. 8.

Figure 9:
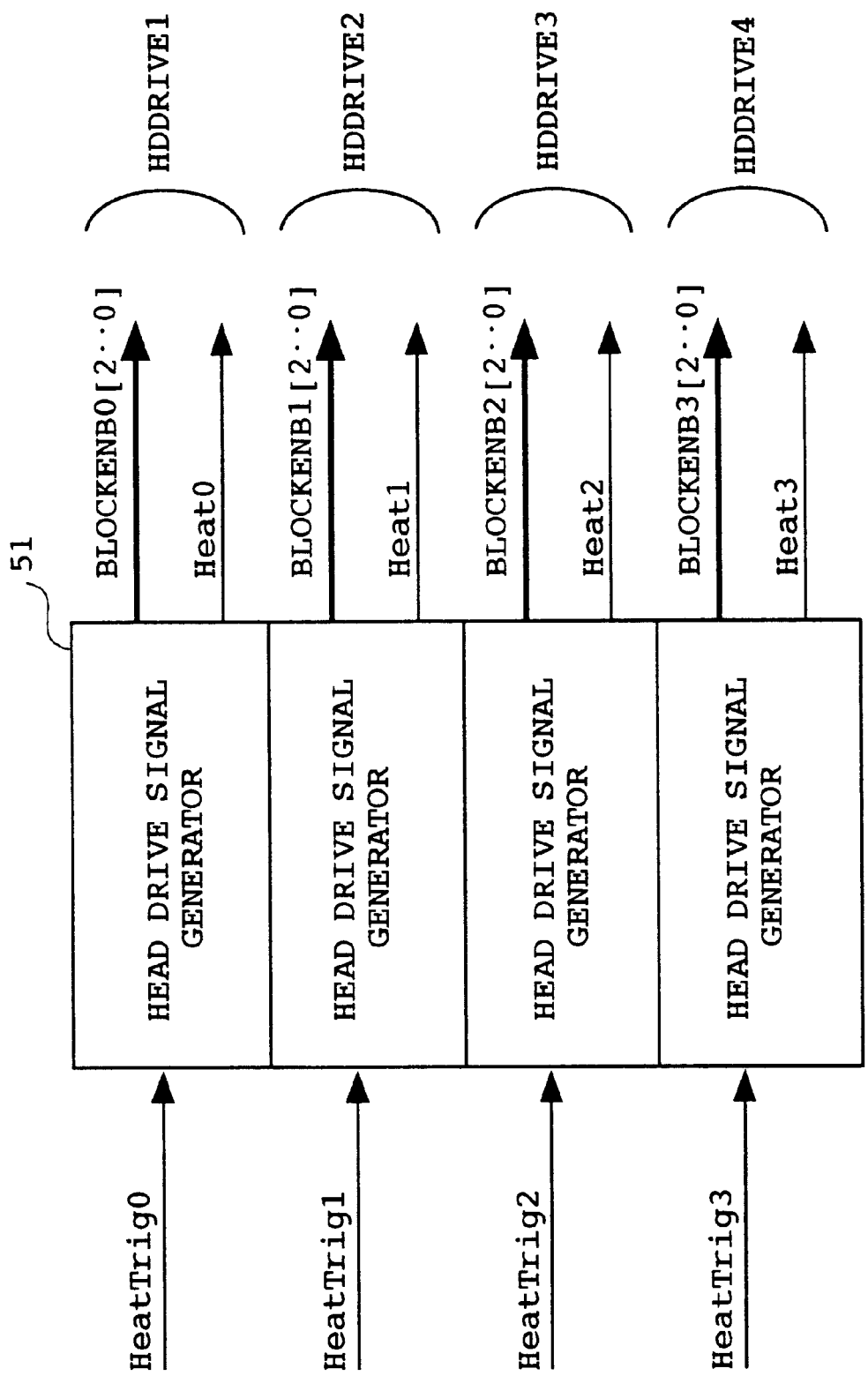
FIG. 9 is an illustration showing the input/output signals of a head drive signal generator 51 shown in FIG. 4.
Figure 10:
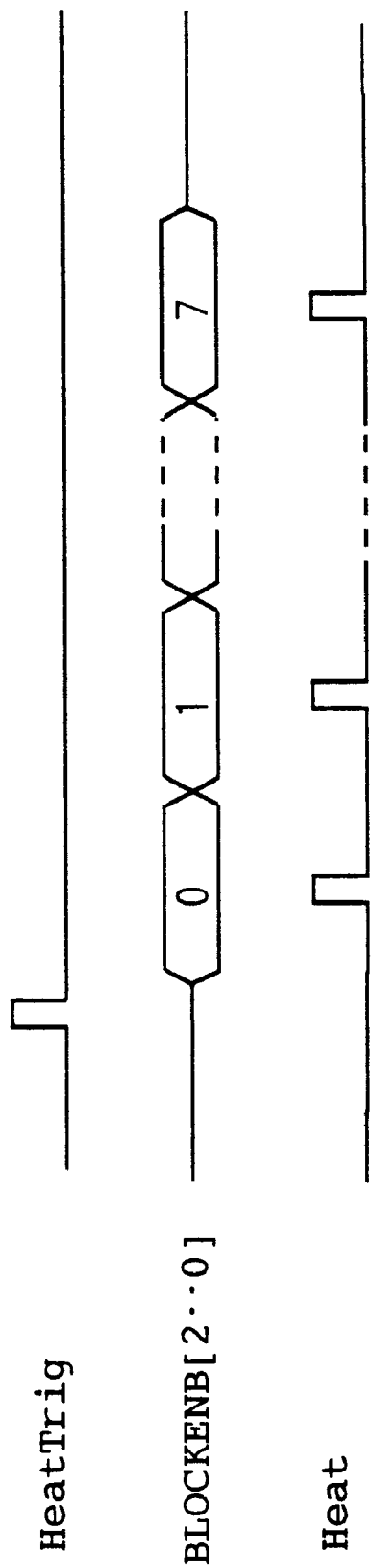
FIG. 10 is a timing diagram showing the relation of the signals of the head drive signal generator 51 shown in FIG. 9.

The print timing generator 43, shown in FIG. 4, selects a latch clock HDLTCLK based on the head selection signal HDSEL to output the heat trigger signals HeatTrig0–HeatTrig3. These signals are used as trigger signals to cause the head drive signal generator 51 to generate the head drive signals HDDRIVE1–HDDRIVE4. As shown in FIG. 9, the head drive signal generator 51 generates three-bit BLOCKENB signal and one-bit Heat signal for each head as HDDRIVE signals. FIG. 10 is a timing diagram showing the relation of these signals. BLOCKENB is a signal used to sequentially drive eight blocks into which 128 nozzles are divided.

The head data buffer 44 shown in FIG. 4 is configured so that the head data HDDATA selected by the head selection signal HDSEL is output therefrom in synchronization with the head transfer clock HDCLK. In this embodiment, each time head data is selected, 32 HDCLK signals are output. That is, 32 bits of data are output. Thus, when data is selected four times, 128 bits (one head) of data are output. The numbers labeled in the head data HDDT (HDDATA) signal at the bottom of FIG. 5 correspond to print nozzle numbers. Print data, composed of 128 bits corresponding to 128 nozzles of each head, are divided into four, 1–32, 33–64, 65–96, and 97–128, and respective division data is transferred using four subsections assigned to that particular head.

Figure 11:
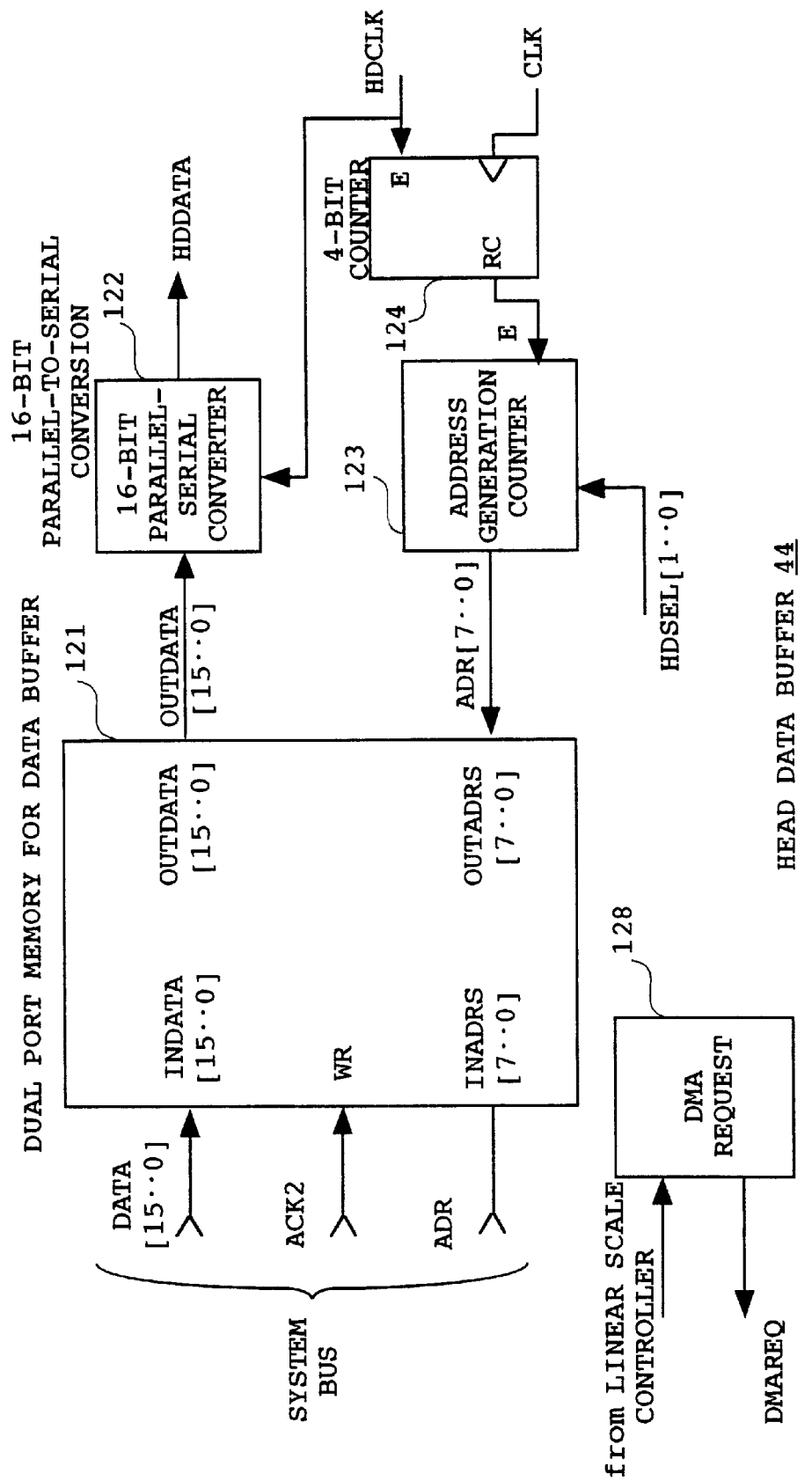
FIG. 11 is a block diagram showing an example of the configuration of a head data buffer 44 shown in FIG. 4.
Figure 12:
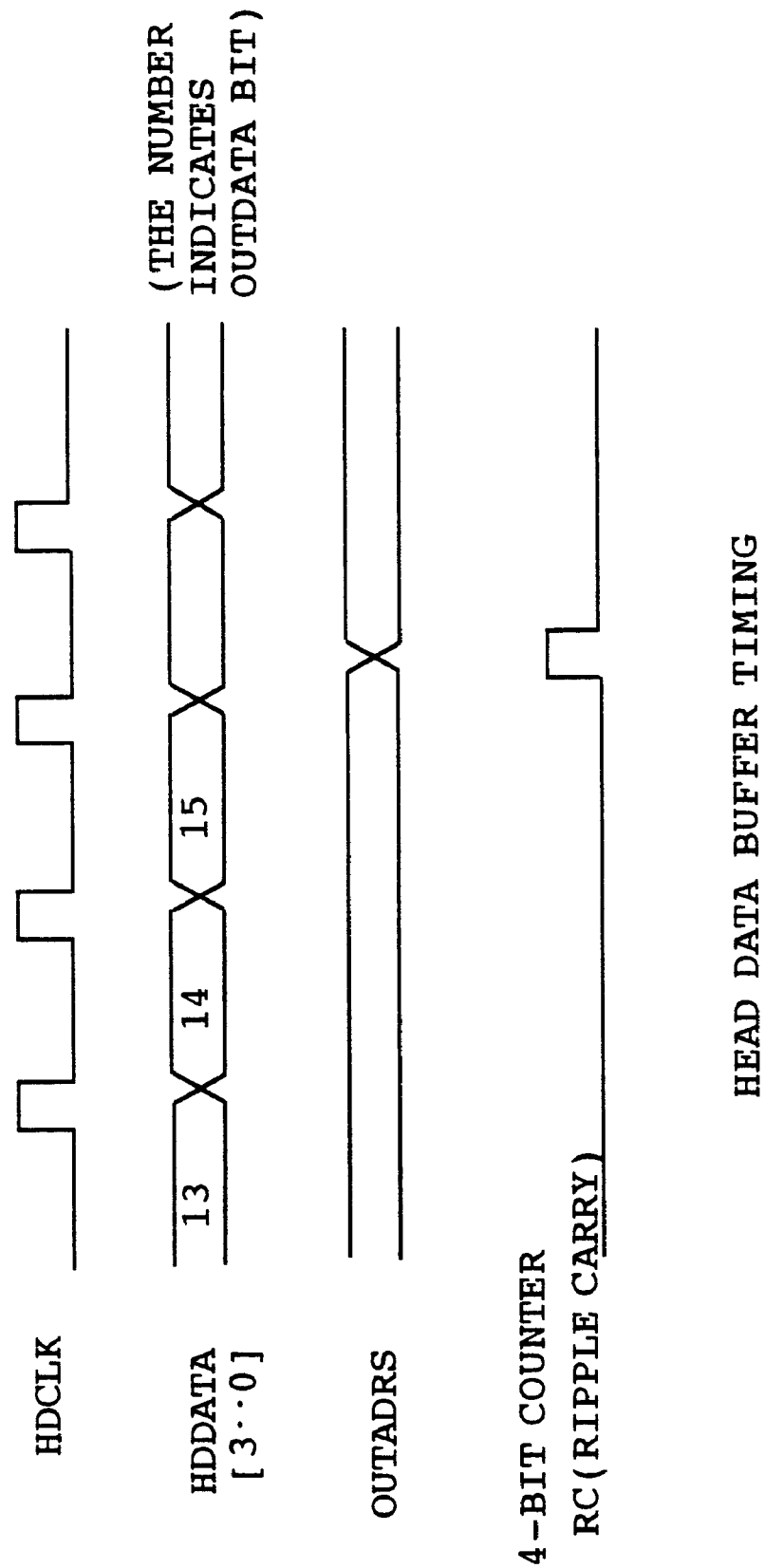
FIG. 12 is a timing diagram showing the operation of the head data buffer 44 shown in FIG. 4.

FIG. 11 shows an example of the configuration of the head data buffer 44 shown in FIG. 4. This buffer comprises a dual port memory 121, a 16-bit parallel-serial converter 122, an address generation counter 123, a four-bit counter 124, and a DMA request issuer 128. In this example, the dual port memory 121 is composed of 256 asynchronous 16-bit words. By setting the DMA request start timing into the DMA request issuer 128 by the MPU, an image data request (REQ2) is generated at an arbitrary carriage position. In synchronization with this signal, the MPU writes one slice of data into the dual port memory 121. Also, in synchronization with HDCLK, data at the address indicated by the address generation counter 123 is read as 16-bit OUTDATA, which is output as serial head data HDDATA via the 16-bit parallel-serial converter 122. The timing diagram in FIG. 12 shows the operation of the head data buffer 44. As shown in the figure, one bit of HDDATA is output each time HDCLK is output. Each time HDCLK is output 16 times, the four-bit counter 124 outputs a Ripple Carry (RC). In response to this signal, the output from the address generation counter 123 to the OUTADRS of the memory 121 is updated.

Figure 13:
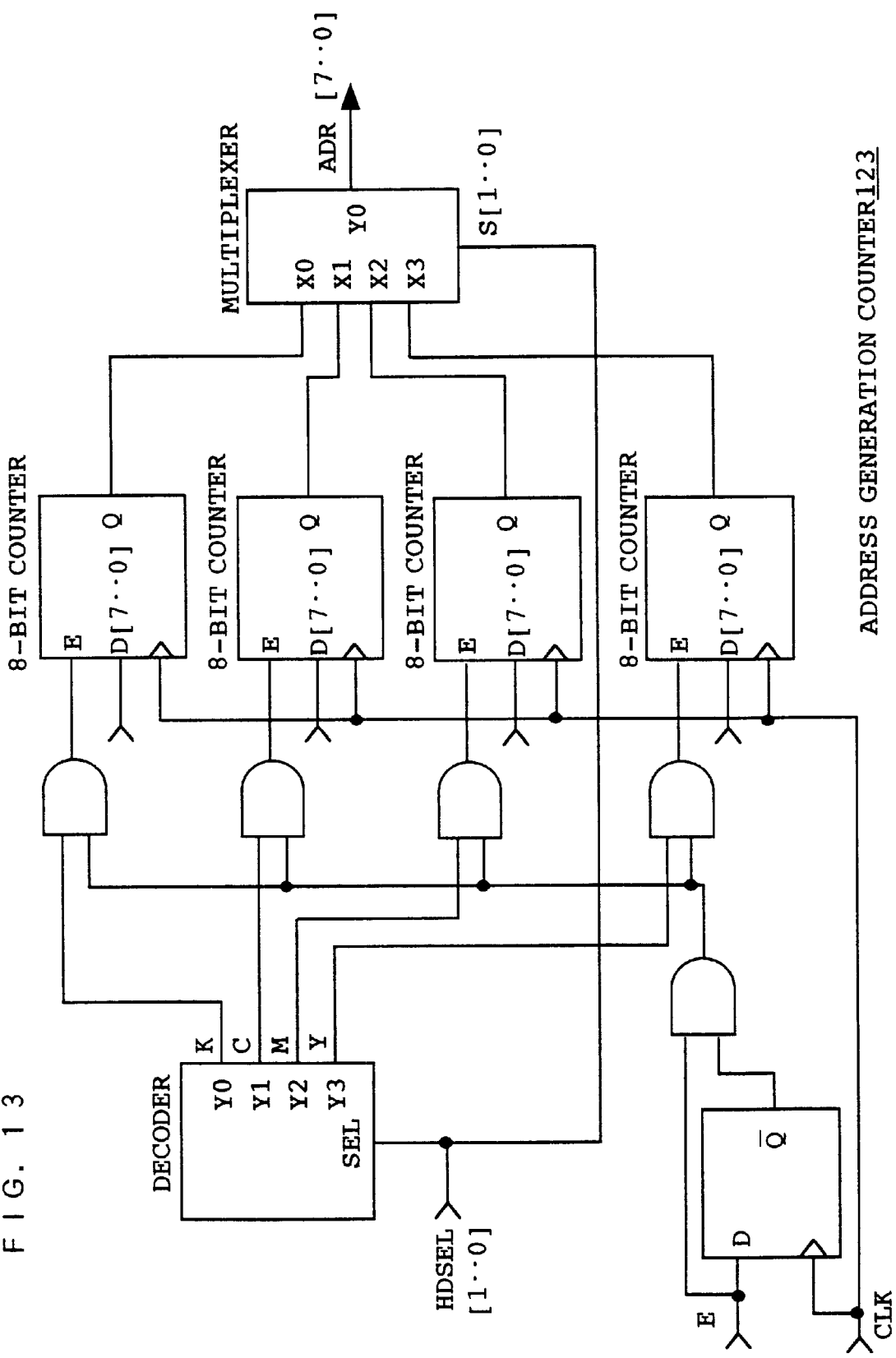
FIG. 13 is a block diagram showing an example of the configuration of an address generation counter 123 shown in FIG. 11.

FIG. 13 shows an example of the configuration of the address generation counter 123 shown in FIG. 11. This circuit comprises four eight-bit counters each of which generates an address for each head in response to the HDSEL signal, a decoder which selectively activates these counters, and a multiplexer which selects the output of one of the counters and outputs it as the address ADR. To determine the address range of each head data, the count increment and the initial address may be set.

Figure 14:
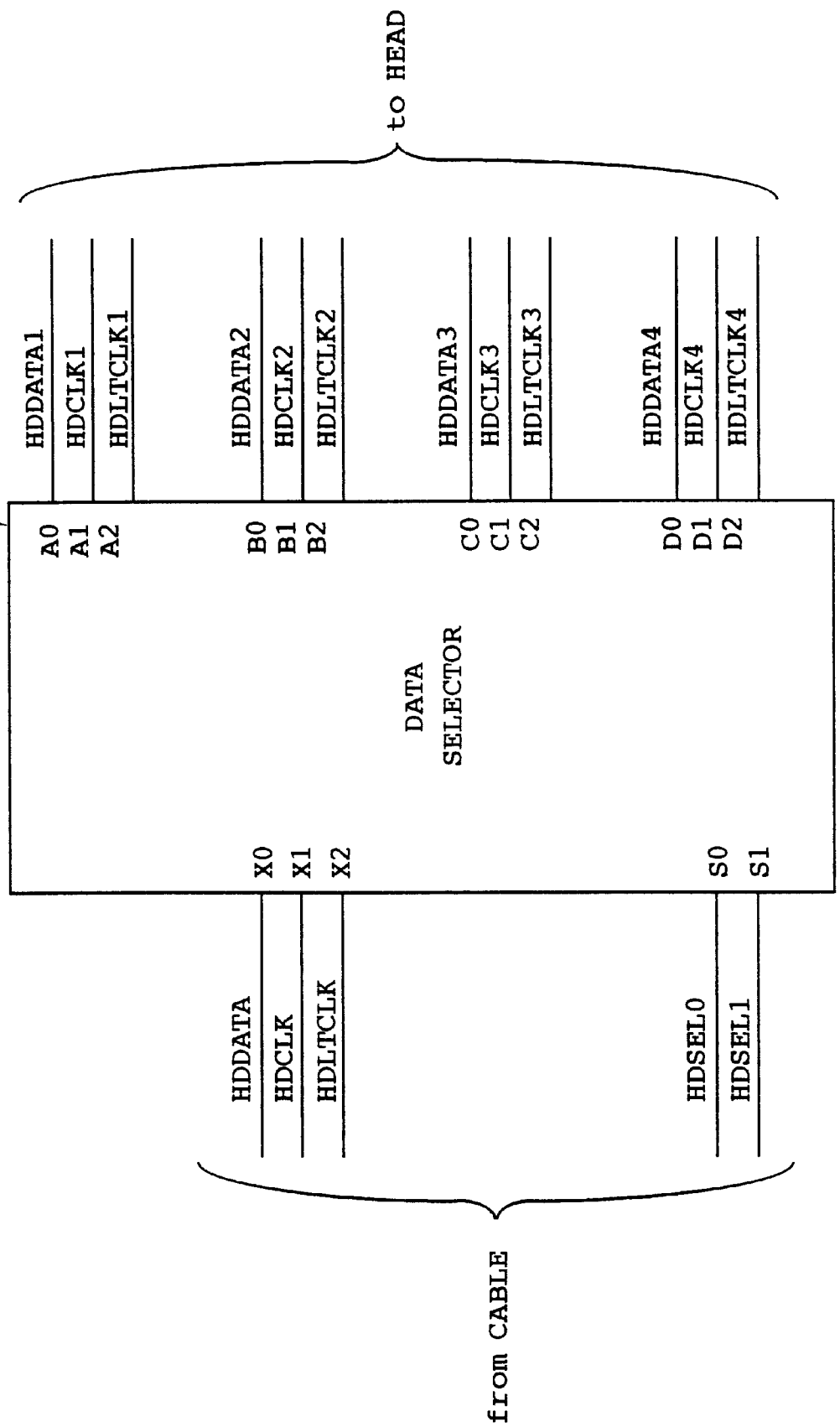
FIG. 14 is an illustration of the input/output signals of a data selector 91 installed in the carriage 12 shown in FIG. 3.

The signal output from the head controller 25, shown in FIG. 3, is sent to the carriage 12 via the cable 13. The carriage 12 has a simple data selector (three 2 to 4 selectors) 91 such as the one shown in FIG. 14. Data is sent to the shift register (81 in FIG. 15 which will be described later) of each head via this data selector.

Figure 15:
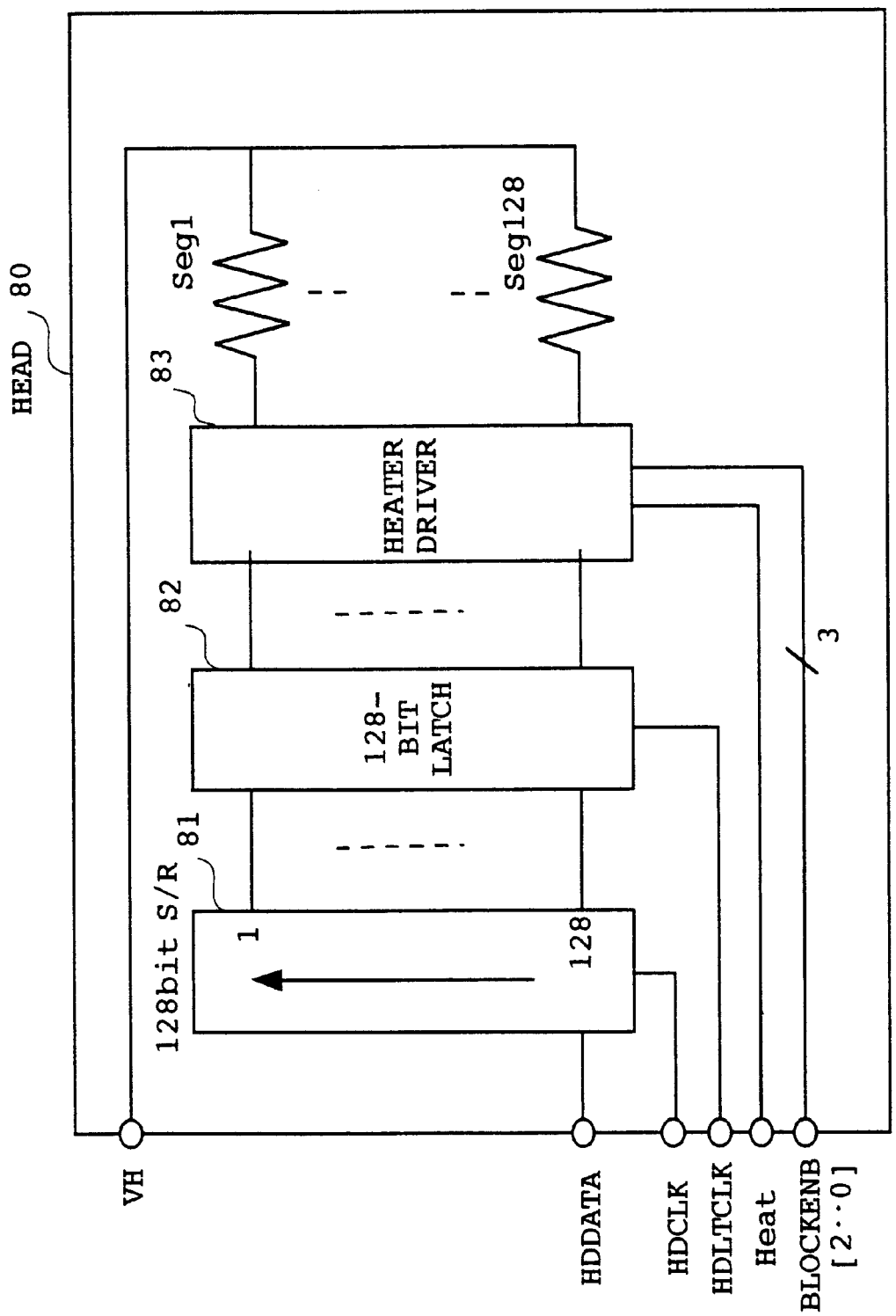
FIG. 15 is a block diagram showing an example of the configuration of an ink jet head in the embodiment of the present invention.

FIG. 15 shows an example of the configuration of an ink jet head 80. The ink jet head 80 comprises a 128-bit shift register 81, a 128-bit latch 82, a heater driver 83, and heaters Seg1-Seg128. The 128-bit shift register 81 serially receives head data HDDATA in response to the HDCLK. When 128 bits of data are received, they are sent to the 128-bit latch 82 in response to the HDLTCLK signal. Depending upon the logical product (ANDing operation) of this data and BLOCKENB, each heater is driven at the timing indicated by the Heat signal.

Figure 16:
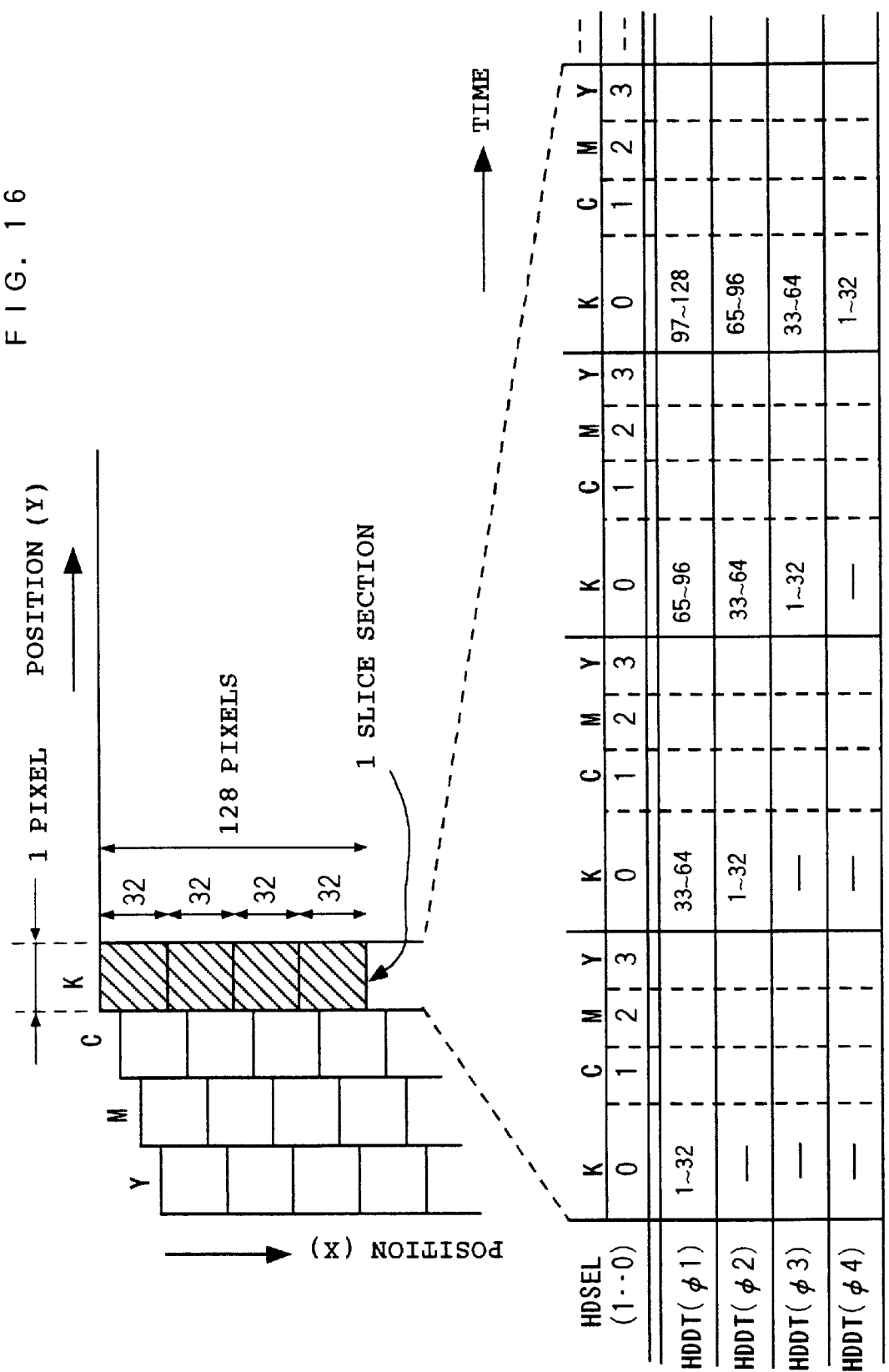
FIG. 16 is an illustration of print timing adjustment in 1/4 pixel increments in the embodiment of the present invention.
Figure 17:
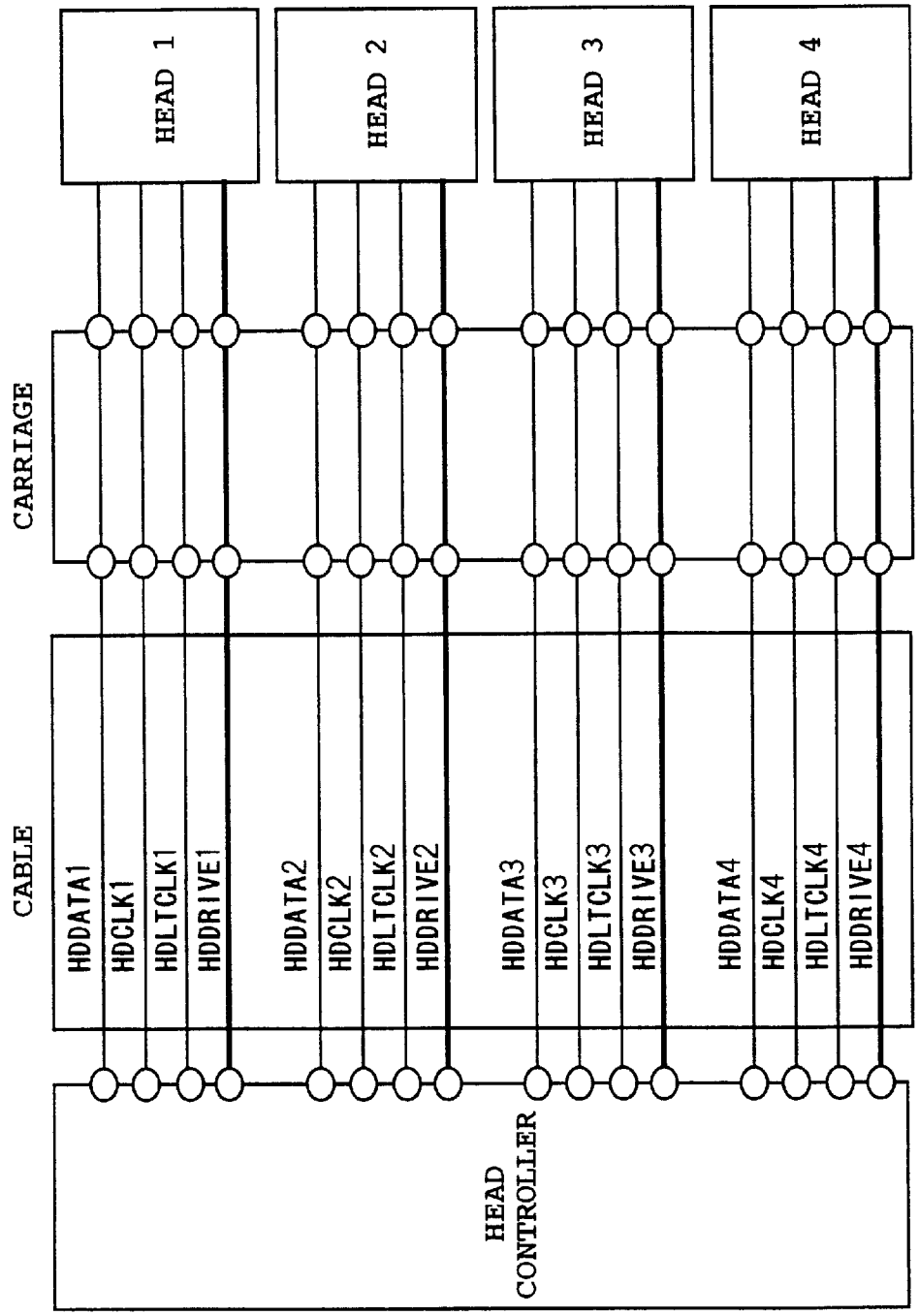
FIG. 17 is an illustration of a first example of the conventional connection between the engine controller and the carriage.

Print timing adjustment that can be made in 1/4 pixel increments in this embodiment will be described with reference to FIG. 16. The upper half of FIG. 16 shows the arrangement of print image pixels. The bottom half shows the relation between the HDSEL signal and the head data HDDT (HDDATA) similar to that shown in FIG. 5. However, this example shows four possible different timings (phases φ1 to φ4) for printing the head data HDDT. As described above, 128 bits of data are transferred for each color of one horizontal slice period. At this time, the one-slice period is divided into four and each divided period is further divided into four subsections to provide a transfer period for each 32 bits. On the other hand, the rising timing can be set for each window signal Wind in 1/4 pixel increments. This setting allows the transfer of data for one color (K in FIG. 16) to be performed in any of four different print timings (phases φ1 to φ4). In addition, the print timing for one color data may be set independently of that for another color data.

Although a head with 128 print nozzles is used in the embodiment described above, the present invention is not limited to this head configuration. For example, for a 160-nozzle head, 40 bits are transferred for each HDSEL and one head of data is transferred in four transfer times. The circuit for such alternation may be configured easily based on the circuit configuration in the embodiment described above. Other print heads may also be used. In the above embodiment, the head data (HDDT) is transferred via one serial signal line. To reduce the HDCLK frequency, parallel signals (about 2–4 bits) may also be used.

Figure 20:
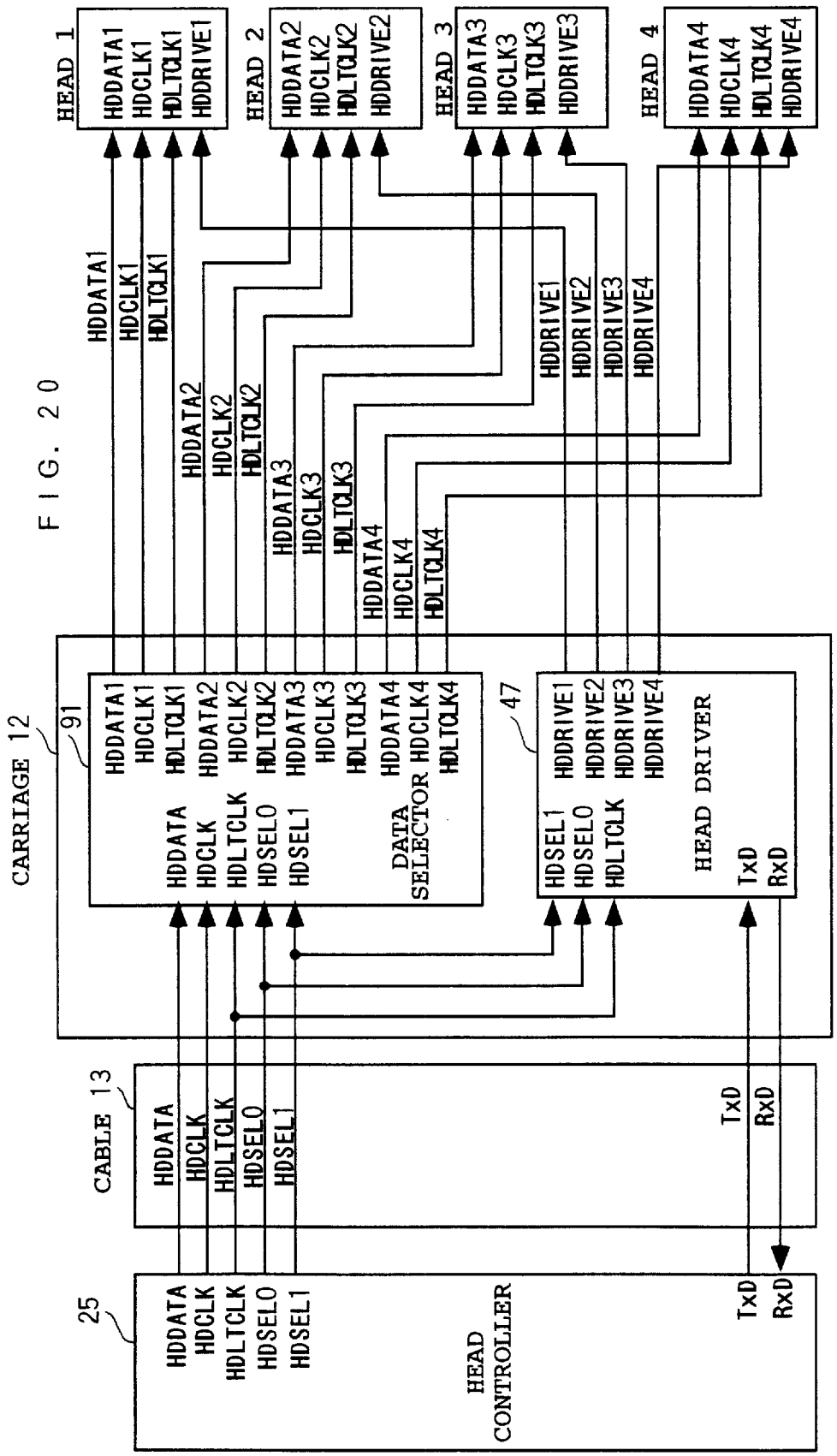
FIG. 20 is a block diagram showing the configuration of a printing apparatus in another embodiment of the present invention in which the head driver is provided in the carriage side.

The head drive signal generator 51 shown in FIG. 9 is located on the head controller 25 side in the above embodiment (see FIG. 4) because the component is a relatively large circuit. However, the head drive signal generator 51, as well as the print timing generator 43, may also be provided on the carriage 12 side as a head driver 47, as shown in FIG. 20. This configuration further reduces the number of signal lines in the cable.

Figure 21:
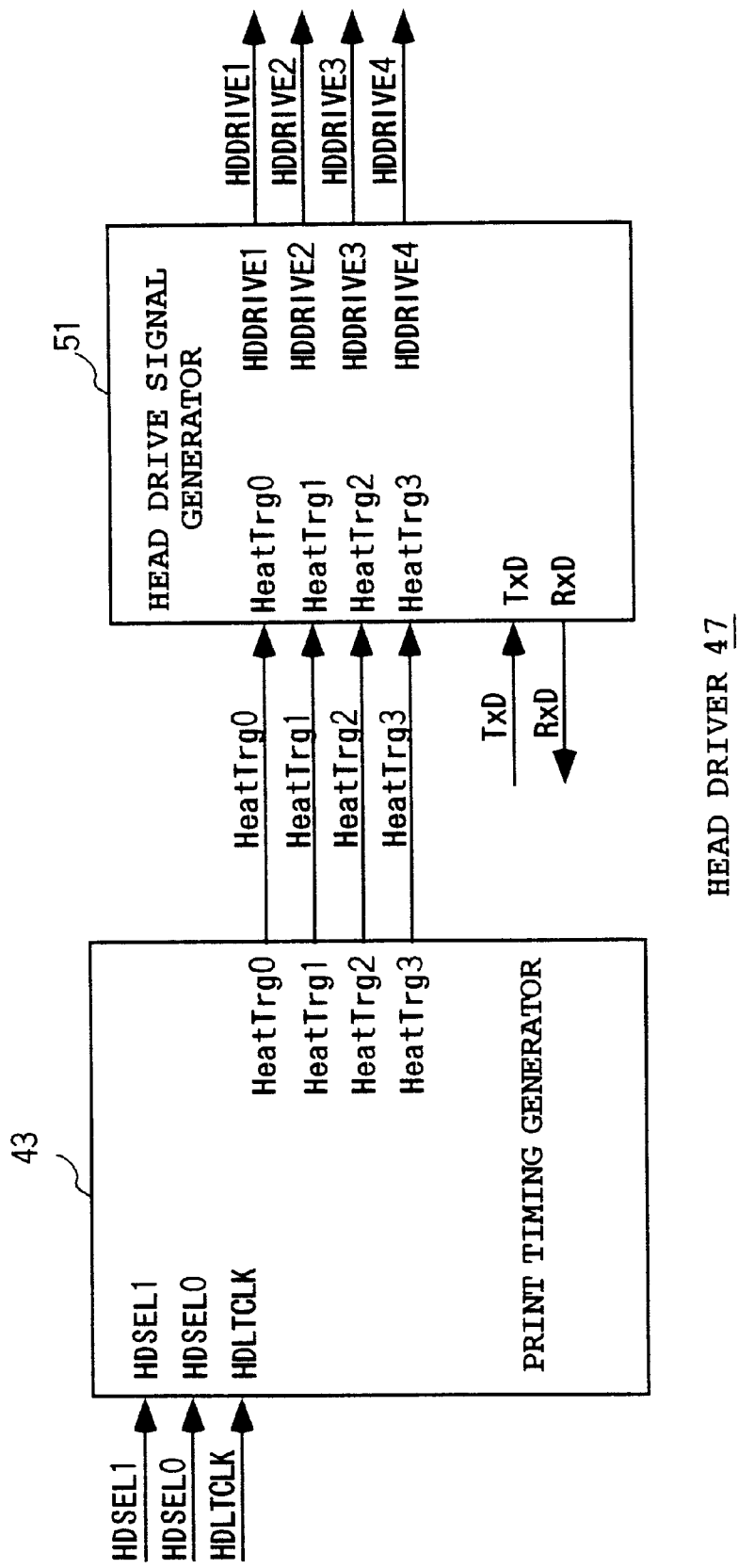
FIG. 21 is a block diagram showing an example of the configuration of the head driver shown in FIG. 20.
Figure 22:
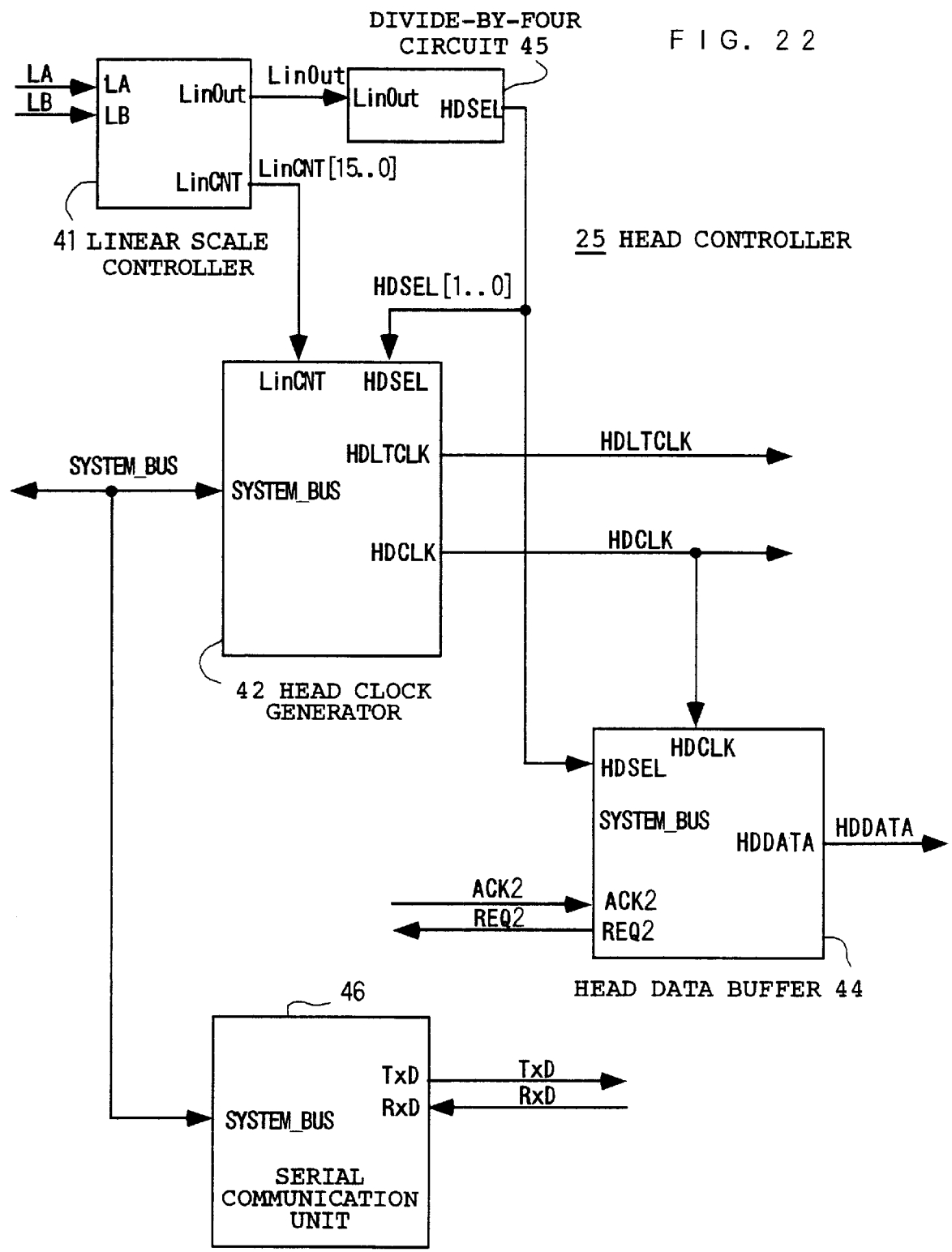
FIG. 22 is a block diagram showing an example of the configuration of the head controller corresponding to the embodiment shown in FIG. 20.

FIG. 21 shows an internal configuration of the head driver 47. The head driver 47 comprises the print timing generator 43 and the head drive signal generator 51 as in the head controller shown in FIG. 4. In this example, however, the head drive signal generator 51 controls, in response to an instruction from the MPU, the pulse width of the pulse signal (Heat signal in FIG. 10) that drives the head. Therefore, the head drive signal generator has the transmitting and receiving terminals (TxD, RxD) for serial communication with the MPU. For communication with these terminals, the head controller 25 has a serial communication unit 46 connected to the MPU system bus as shown in FIG. 22. Communication with the head drive signal generator 51 described above is made via the transmitting and receiving terminals (TxD, RxD) of the serial communication unit 46.

Comparison between the cable 13 in FIG. 20 and the cable 13 in FIG. 3 indicates that the configuration shown in FIG. 20 further reduces the number of signal lines. This configuration is preferable when the carriage 12 has an additional room for installing the head driver 47.

A printing apparatus according to the present invention reduces the number of signal lines of the cable between the engine controller and the carriage on which the print heads are carried. In addition, the logical circuits installed in the carriage may comprise only logical gates not requiring the system clock, requiring less countermeasures against radiation noise and so on.

INDUSTRIAL APPLICABILITY

The present invention is applicable to the research and development, and the manufacturing of a printing apparatus such as a printer and a plotter.

What is claimed is:

1. A method for transferring print data from a controller to a carriage via a cable in a printing apparatus which performs printing while moving the carriage bi-directionally over a sheet of paper, said carriage carrying thereon a plurality of print heads each having a plurality of dot printing elements;

wherein said cable comprises at least a signal line via which serial print data to be supplied to said plurality of print heads is transferred in a predetermined order, a signal line via which a clock signal corresponding to individual bits of the serial print data is transferred, and signal lines via which a signal indicating which print head corresponds to which print data included in the serial print data is transferred, said method comprising the steps of:

dividing one slice section into a plurality of sections, said slice section corresponding to a time slot required to transfer a unit of print data corresponding to the plurality of dot printing elements of the plurality of heads and further dividing each divided section into a number of subsections, said number being equal to the number of said print heads;

assigning the different subsections of each divided section to said plurality of print heads;

dividing the unit of print data for each print head into the number of the plurality of divided sections; and starting a transfer of the print data of each print head independently of the print data of other print heads, beginning with any one of the plurality of subsections assigned to that particular print head in one divided section.

2. The method for transferring print data according to claim 1, wherein four print heads are used as said plurality of print heads, said one slice section is divided at least into four divided sections, and each divided section is further divided into four subsections.

3. The method for transferring print data according to claim 1, wherein drive signals of respective heads are generated in said controller and said cable further comprises the drive signals for the respective heads.

4. The method for transferring print data according to claim 1, wherein drive signals of respective heads are generated in said carriage and said cable further comprises a signal for transferring serial data for controlling a pulse width of the drive signal of each head.

5. A printing apparatus which performs printing while moving a carriage bi-directionally over a sheet of paper, said carriage carrying thereon a plurality of print heads each having a plurality of dot printing elements, said printing apparatus comprising:

a controller for generating serial print data including print data for said plurality of print heads in a predetermined order, a clock signal corresponding to individual bits of the serial print data, a signal indicating which print head corresponds to which print data included in the serial print data, and a drive signal of each head;

a cable for transferring the serial print data and various signals generated by said controller to said carriage; and a signal distributing means for distributing the print data and the various signals received from said cable to said plurality of print heads, said signal distributing means being provided in said carriage;

wherein said controller divides one slice section into a plurality of sections, said slice corresponding to a time slot required to transfer a unit of print data corresponding to the plurality of dot printing elements of the plurality of heads; further divides each divided section into a number of subsections, said number being equal to the number of said print heads; assigns the different subsections of each divided section to said plurality of print heads; divides the unit of print data for each print head into the number of the plurality of divided sections; and starts a transfer of the print data of each print head independently of the print data of other print heads, beginning with a specified subsection of the plurality of subsections assigned to that particular print head in one slice section.

6. The printing apparatus according to claim 5, wherein four print heads are used as said plurality of print heads, said one slice section is divided at least into four divided sections, and each divided section is further divided into four subsections.

7. The printing apparatus according to claim 5, wherein each print head has a plurality of dot print means arranged in a direction substantially perpendicular to a carriage moving direction and wherein the print data for said plurality of dot print means of one print head is transferred using said plurality of subsections assigned to that particular print head.

8. A printing apparatus which performs printing while moving a carriage bi-directionally over a sheet of paper, said carriage carrying thereon a plurality of print heads each having a plurality of dot printing elements, said printing apparatus comprising:

a controller for generating serial print data including print data for said plurality of print heads in a predetermined order, a clock signal corresponding to individual bits of the serial print data, and a signal indicating which print head corresponds to which print data included in the serial print data;

a cable for transferring the serial print data and various signals generated by said controller to said carriage;

a signal distributing means for distributing the print data and the various signals received from said cable to said plurality of print heads, said signal distributing means being provided in said carriage; and a drive signal generating means for generating the drive signal of each head, said drive signal generating means being provided in said carriage;

wherein said controller divides one slice section into a plurality of sections, said slice corresponding to a time slot required to transfer a unit of print data corresponding to the plurality of dot printing elements of the plurality of heads; further divides each divided section into a number of subsections, said number being equal to the number of said print heads; assigns the different subsections of each divided section to said plurality of print heads; divides the unit of print data for each print head into the number of the plurality of divided sections; and starts a transfer of the print data of each print head independently of the print data of other print heads, beginning with a specified subsection of the plurality of subsections assigned to that particular print head in one slice section.

9. The printing apparatus according to claim 8, wherein four print heads are used as said plurality of print heads, said one slice section is divided at least into four divided sections, and each divided section is further divided into four subsections.

10. The printing apparatus according to claim 8 wherein each print head has a plurality of dot print means arranged in a direction substantially perpendicular to a carriage moving direction and wherein the print data for said plurality of dot print means of one print head is transferred using said plurality of subsections assigned to that particular print head.

11. The printing apparatus according to claim 8, wherein said drive signal generating means comprises means for adjusting a pulse width of the drive signal of each head and wherein said cable further comprises a serial data transfer signal line for controlling the pulse width of the drive signal of each head.

* * * * *